United States Patent [19]
Chalifoux

[11] Patent Number: 5,458,488
[45] Date of Patent: Oct. 17, 1995

[54] DENTAL IMPLANT AND POST CONSTRUCTION

[75] Inventor: Paul R. Chalifoux, Wellesley, Mass.

[73] Assignee: Wellesley Research Associates, Inc., Wellesley, Mass.

[21] Appl. No.: 194,415

[22] Filed: Feb. 10, 1994

Related U.S. Application Data

[63] Continuation-in-part of Ser. No. 75,809, Jun. 14, 1993, which is a continuation-in-part of Ser. No. 896,602, Jun. 10, 1992, Pat. No. 5,312,253, which is a continuation-in-part of Ser. No. 814,507, Dec. 30, 1991, Pat. No. 5,197,881.

[51] Int. Cl.⁶ .................................................. A61C 8/00
[52] U.S. Cl. .................................................. 433/173
[58] Field of Search .................................. 433/172, 173, 433/174, 175, 176

[56] References Cited

U.S. PATENT DOCUMENTS

| | | | |
|---|---|---|---|
| 4,447,210 | 5/1984 | Hidaka et al. | 433/173 |
| 4,850,870 | 7/1989 | Lazzara et al. | 433/173 |
| 4,850,873 | 7/1989 | Lazzara et al. | 433/173 |
| 4,938,694 | 7/1990 | Ledermann | 433/174 |
| 5,006,069 | 4/1991 | Lazzara et al. | 433/173 |
| 5,009,596 | 4/1991 | Soderberg | 433/174 |
| 5,292,252 | 3/1994 | Nickerson et al. | 433/173 |

Primary Examiner—Cary E. O'Connor
Attorney, Agent, or Firm—Paul J. Cook

[57] ABSTRACT

A dental post-dental implant system is provided wherein the post is provided with a circumferential collar that mates with an upper portion of a circumferential wall of the implant. The circumferential collar resists expansion of the implant after being positioned in a patient.

6 Claims, 4 Drawing Sheets

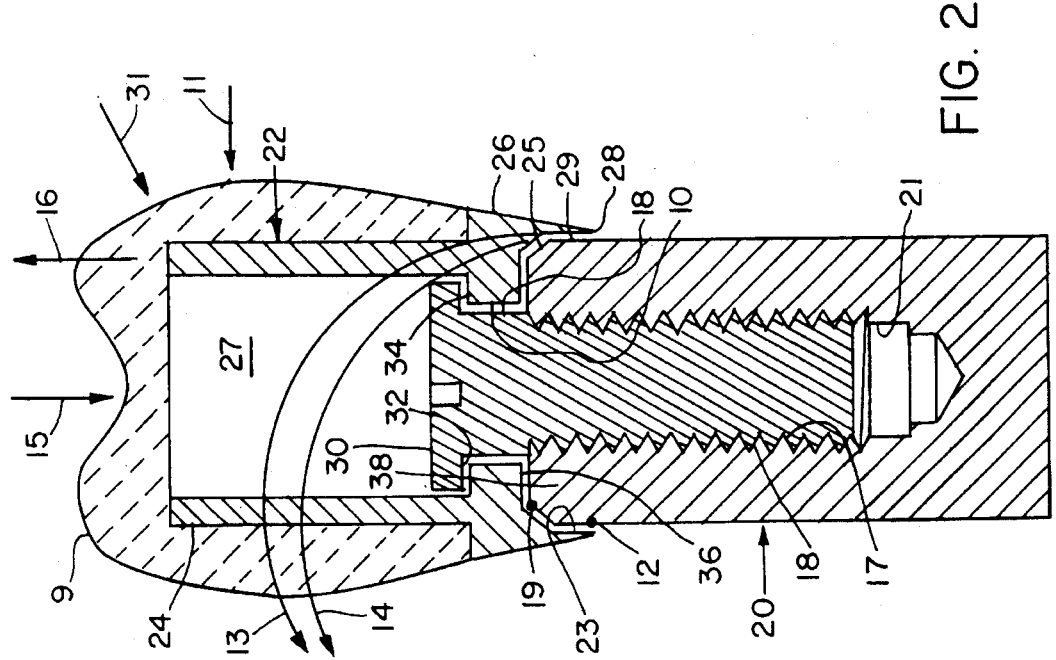
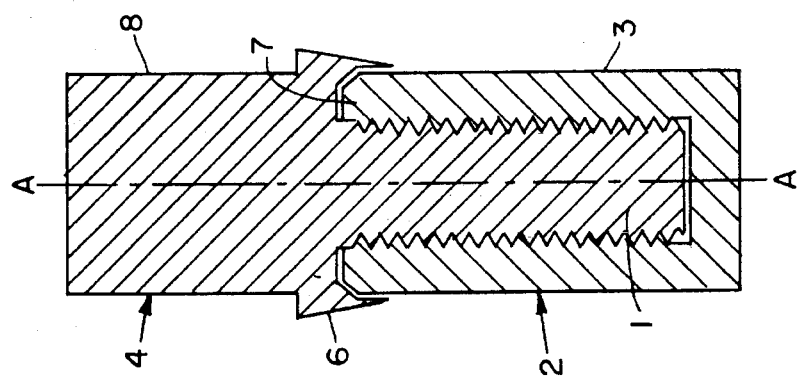

DENTAL IMPLANT AND POST CONSTRUCTION

REFERENCE TO RELATED APPLICATIONS

This application is a continuation-in-part of application Ser. No. 08/075,809, filed Jun. 14, 1993, pending, which in turn, is a continuation in part of application Ser. No. 896,602, filed Jun. 10, 1992, now U.S. Pat. No. 5,312,253, which, in turn, is a continuation-in-part of application Ser. No. 814,507, filed Dec. 30, 1991, now U.S. Pat. No. 5,197,881.

BACKGROUND OF THE INVENTION

This invention relates to a dental implant system which can be inserted into the jaw bone of a patient and can be utilized to improve retention of a dental restoration built onto the jaw bone.

Presently, dental implant systems are utilized to fix a synthetic tooth structure to the jaw bone of a patient in order to replace a missing tooth. The implant system includes an implant which is inserted into a hole in the patient's jaw bone drilled by a dentist. The implant includes a hole designed to receive a dental post which, in turn, serves to retain a core upon which a tooth crown is built. After the implant is inserted into the jaw bone, it is covered by the patient's gum and allowed to heal from 3–6 months while the bone grows to surround and retain the implant. The gum then is opened to expose the implant. At this time, impressions are made or a post needed to support the crown is positioned into the implant. At the present time, these posts are screwed into place with the implant having a helical path and the post having a mating helical thread. The post bottom can have threads or can have a hollow core for a screw to unite the post and implant. A screw system alone does not provide an antirotation characteristic to the implant system and can unscrew and loosen. When multiple implants are placed to support one prosthesis, a tripod effect is created which minimizes lateral and rotational forces onto individual implants. When only two implants are placed or when multiple implants are placed in a straight line to support a single prosthesis, lateral forces created by functional or parafunctional forces stress posts or screws and cause fracture of an implant fixture and/or the post or screw. Single implants incur these forces and rotational forces.

A problem with this system is that the screws break during implacement and during function. Also, the screws are small and may be dropped in the mouth accidently or they are difficult to place into the back portion of the mouth. In addition, it is difficult to determine if a post is fully seated with a screw system. After the post is positioned in the implant, it extends above the gum so that a dental prosthesis including a core can be retained in place. All single posts must resist normal rotational forces which occur during normal or abnormal functions. In general, preformed posts do not provide good stability against rotational force because they are circular and rotate easily when placed in a circular hole in the implant. Screw type posts can exert large lateral stresses which lead to potential implant fixture fracture and implant loss.

It has been proposed in U.S. Pat. Nos. 4,480,997; 4,490,116 and Re 31,948, to utilize a threaded dental post which is introduced into the bore of a tooth stub by being rotated to thread the post into position. The dental post includes a stem portion having a slot extending through the stem thickness and along its length which renders the stem being formed of two legs each having its outside surface threaded. The outside surface of the legs intimately contact the walls of the bore so that the threads on the legs can engage the walls. In addition, a spring-like connection for the two legs is provided so that a radial outward spring force is applied to the legs to force them against the bore walls. These dental posts are undesirable since a rotational force must be applied to the post to position it properly into the bore. This positioning process is undesirable since it is time consuming and causes the patient discomfort. In addition, the possibility exists that the post will be threaded too far which will result in fracture. Furthermore, the radially outward forces of the legs on the tooth stub can result in fracture of the tooth stub over time. The same problems are present when these posts are used in conjunction with an implant positioned in a jaw bone.

U.S. Pat. No. 1,534,409 discloses a two legged post having corrugated surfaces which fit into a root canal having generally parallel walls. This surface design materially reduces the post surface area which contacts the canal walls and thus post retention relies primarily upon cement adhesive strength.

U.S. Pat. No. 5,030,095 discloses an abutment for a dental implant having a collar that ends in a butt joint have a relative flat angle relative to the vertical dimension of the implant. This arrangement is undesirable since debris will remain on the butt joint surfaces when the abutment and implant are joined together to produce a space into which bacteria can infiltrate.

The post forms a tighter fit to the implant at the outside surface of the implant. Implants fail if there is any opening into which bacteria can form infection. Present implants form a junction by squeezing two flat surfaces together forming a butt joint or horizontal interface. Misalignment of the components or debris such as blood or saliva caught on one of the flat surfaces results in an opening at this critical butt joint. In addition, roughness from machining results in opening such that the greater the roughness the greater the resulting openings.

Accordingly, it would be desirable to provide a dental implant having a bore for a dental post which can be inserted into a hole in the jaw. In addition, it would be desirable to provide a dental implant with means to provide mechanical interaction in order to retain the post in the implant hole while minimizing or eliminating fracturing forces on the implant walls exerted by the post. Furthermore it would be desirable to provide a post which resists rotational forces. Furthermore, it would be desirable to provide a system for utilizing such a dental implant and post system which facilitates the placement of a core and a crown. Furthermore, it would be desirable to provide such a system for joining the prosthesis to the post while avoiding a space into which microorganisms can infiltrate. Furthermore it would be desirable to provide a post which maximizes fit on the post to the implant at the joint area while avoiding a space into which microorganisms can infiltrate. Furthermore it would be desirable to provide a post and implant which minimizes post and implant fracture.

SUMMARY OF THE INVENTION

This invention provides a dental implant utilized in conjunction with a dental post in order to support a dental prosthesis. The implant is sized to be positioned within a hole of the jaw bone of a patient. The implant has an internal hole or bore to permit positioning of a dental post therein. The post is joined to the implant in any manner such as threaded posts, screws, slots and wings, frictional extensions, taper fits, etc. The post is designed such that a portion of the post surrounds an outside top section circumferentially about the implant in a manner which prevents microorganisms infiltration. The top section of the implant comprises that section in which there is the bore hole which accepts a post. The junction between the post and the implant is a vertical joint and can be parallel or slightly tapered depending on the type of fit desired. When force is applied to a prosthesis, the junction on the outside wall of the implant will support the implant to minimize fracture and to further support the post to minimize post fracture.

With a vertical or slightly tapered junction of the post to the implant, material which is on the flat surfaces or roughness from machining on the post or implant surfaces is overcome to always result in a tight fit. For example, if a one millimeter junction of the outside surface of the implant and to a matching post placed is formed, an opening between the flat surfaces on the bottom of the post and the flat surface of the implant top of the implant results in no opening. Even when the opening were one half millimeter between the flat surfaces, there would still be one half millimeter of vertical junction engaging and no opening at the post-implant interface.

In addition, the vertical or slightly tapered junction provides an improved retention of the post in the implant and better resistance to rotational forces.

In an alternative embodiment of this invention, the junction on the implant is beveled at the top surface of the implant to render engagement easier on a true vertical bevel.

In another alternative embodiment of the invention, the vertical junction is tapered such that the circumference of the top surface of the implant where the central bore is positioned, is slightly smaller and continuously wider continuing downward until the end of the junction of the post and implant.

In still another alternative embodiment of this invention, the vertical junction is indented into the side of the implant for improved retention, collar thickness and force resistance.

BRIEF DESCRIPTION OF THE DRAWINGS

FIG. 1 is a cross sectional view of an implant and post of this invention.

FIG. 2 is a cross sectional view of an alternative implant and post of this invention.

DESCRIPTION OF SPECIFIC EMBODIMENTS

Figure 5:
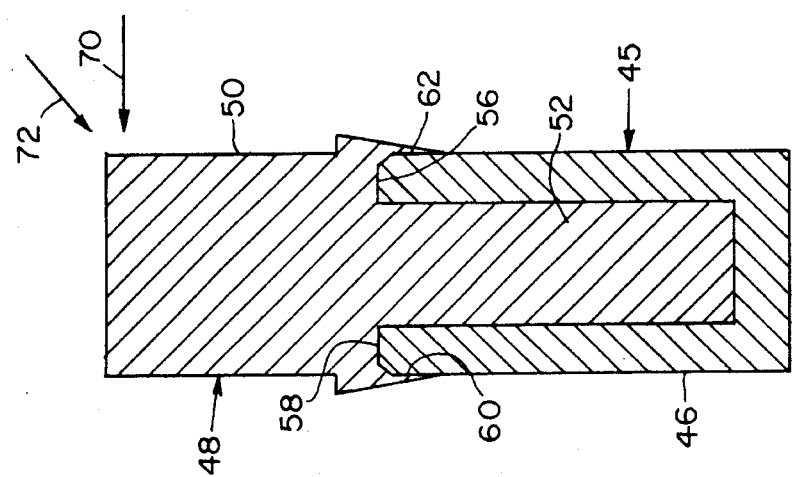
FIG. 5 is a cross sectional view of the post and implant of FIG. 3 fully assembled.

The dental implant of this invention includes a bore having a means for joining a post such as threads, slots, extensions, frictional tapers, or the like. The post of this invention includes a stem which joins the post to the implant, a top section which accepts a prosthesis and a collar which circumferentially surrounds and mates with the outside surface of the implant. The collar section of the post provides an exact fit to the implant. In an alternative embodiment, a slightly smaller fit is provided which causes the post collar section to expand thereby providing a tight fit to the implant.

The collar on the post matching to the outside surface of the implant defines a definite path of withdrawal of the post from the implant straight up. Forces straight up which tend to dislodge the post are resisted by the stem portion of the post positioned into the implant and by any frictional contact of the collar against the implant. Forces which are directed downward are resisted by the usual components of the post including the shoulder area and the bottom of the post stem section against the bottom of the implant bore. All lateral forces which are angled relative to the long axis of the post and therefore path of withdrawal of the post are resisted by the post stem section against the walls of the bore of the implant and the collar against the outside surface of the implant. Rotational forces are resisted by friction components of the post collar against the implant in addition to the usual use of internal squares, polygons, ovals, extensions, slots or the like.

In one embodiment, the post collar is not circular but oval matching an oval implant outside shape therefore providing improved resistance to rotational forces.

In still another embodiment, the post collar is expanded into position. The collar starts at a fixed diameter with the matching implant diameter being larger. The collar is made sufficiently thin as measured against its elasticity that it can be stretched over the implant for a tight fit.

In still another embodiment, the post collar is beveled such that the engaging lowest section of the collar has a greater internal diameter than the engaging upper section. The implant is constructed to have a matching portion such that the top section of the implant has a smaller outside diameter which increases in diameter down the implant at least to the end of the area of engagement of the implant with the post collar.

In still another embodiment, the vertical junction is indented into the side of the implant for improved retention, collar thickness and force resistance.

The outside surface of the implant which mates with an inside surface of the circumferential collar is positioned at an angle to the vertical dimension of the implant between about 0 degrees and 25 degrees, preferably between about 0 and 10 degrees, most preferably about 0 degrees to 5 degrees. The outside surface of the implant which mates with the inside surface of the post intersects the remaining outside surface of the implant or forms a continuous surface of the implant (0 degrees) thereby to avoid a butt surface on which debris or the like can be retained to form an undesirable space. Since the post inside surface is moved downward toward the implant when positioned, it positions all debris or the like away from any space between the post and the implant.

Referring to FIG. 1, the dental implant 2 having an axis A—A is made of any suitable dental material includes top section 7 and a bottom section 3. Post 4 includes a top section 8 and stem section 1 which is threaded securely into implant 2. Post 4 includes collar section 6 which fits securely over and circumferentially around top section 7 of implant 2 and a flange section 5.

Referring to FIG. 2, the dental implant 20 has central bore 21 which accepts screw 30. Post 22 has top section 24 and a circumferential collar 26. Artificial tooth 9 is placed over post 22. Post 22 is placed onto implant 20 such that bottom 28 of collar 26 engages bevel 25 of a circumferential wall of implant 20 and slides down onto outside surface 29 of implant 20. Screw 30 is passed through bore 27 of post 22 and threaded into central bore 21 of implant 20. Screw 30 is tightened such that bottom surface 32 of screw 30 engages surface 34 of post 22 and bottom surface 36 of post 22 engages top surface 38 of implant 20. As tightening of screw 30 is effected, bottom 28 of collar 26 slides down outside wall 29 of implant 20 and internal wall 23 of collar 26 engages wall 29 of implant 20.

When forces as the result of function or parafunction are applied, different areas of resistance occur. Compression force 15 is resisted by bottom surface 36 of post 22 pressing against top surface 38 of implant 20. Dislodging force 16 is resisted by surface 34 of post 22 pressing against surface 32 of screw 30 and the threads of screw 30 against the threads of implant 20. Forces which occur at any angle other than force 15 or force 16 are shearing forces as exemplified by forces 11 and 31. With no collar 26 to interact with outside surface 29 of implant 20, shear force 31 forms a circular rotational force 13 with a fulcrum about point 19. Resistance to this force occurs as surface 34 of post 22 presses against wall 32 of screw 30 as rotational forces are translated upward. Resistance is further accomplished by surface 10 of post 22 pressing against threads and side wall 18 of screw 30. Excessive force, excessive continuing intermittent forces and stress fatigue will lead to screw fracture. Resistance further occurs as the outside surface 18 of screw 30 presses against bore wall 17 of implant 20. Excessive force therefore causes implant fixture fracture.

With collar 26 engaging outside surface 29 of implant 20, force distribution and resistance changes. The same resistance factors as describe in the previous paragraph apply, however, additional resistance occurs. Force 31 is translated into circular rotational force 14 drawn around new fulcrum point 12 and drawn with diameter to point 28. Because the top outside surface 29 of implant 20 is wider and therefore falls outside the rotational arc 14, resistance is formed by surface 23 of collar 26 of post 22 pressing against outside surface 29 of implant 20. This additional resistance results in less force applied to the implant surface 17 and surface 32 and 18 of screw 30 therefore resulting in less chance of screw or implant fracture. In addition, surface 18 of screw 30 is pressing against wall 17 of implant 20 which results in wall 29 of the implant pressing against surface 23 on the inside of collar 26 of post 22 therefore providing more resistance to implant fracture.

Figure 4:
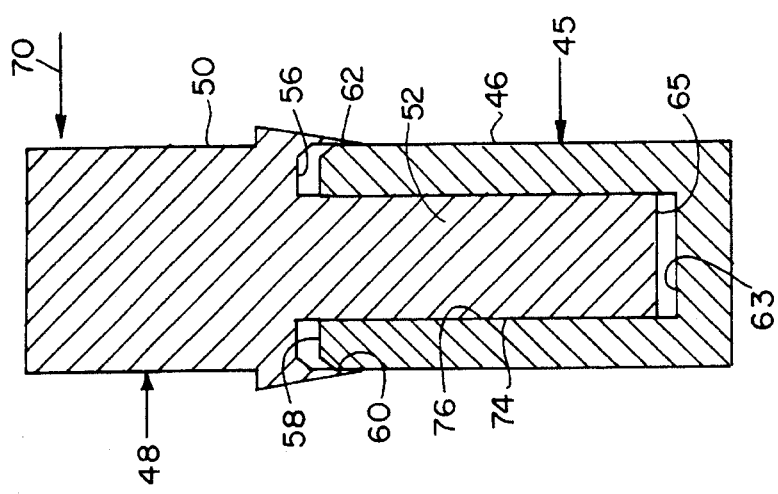
FIG. 4 is a cross sectional view of the post and implant of FIG. 3 partially assembled.
Figure 3:
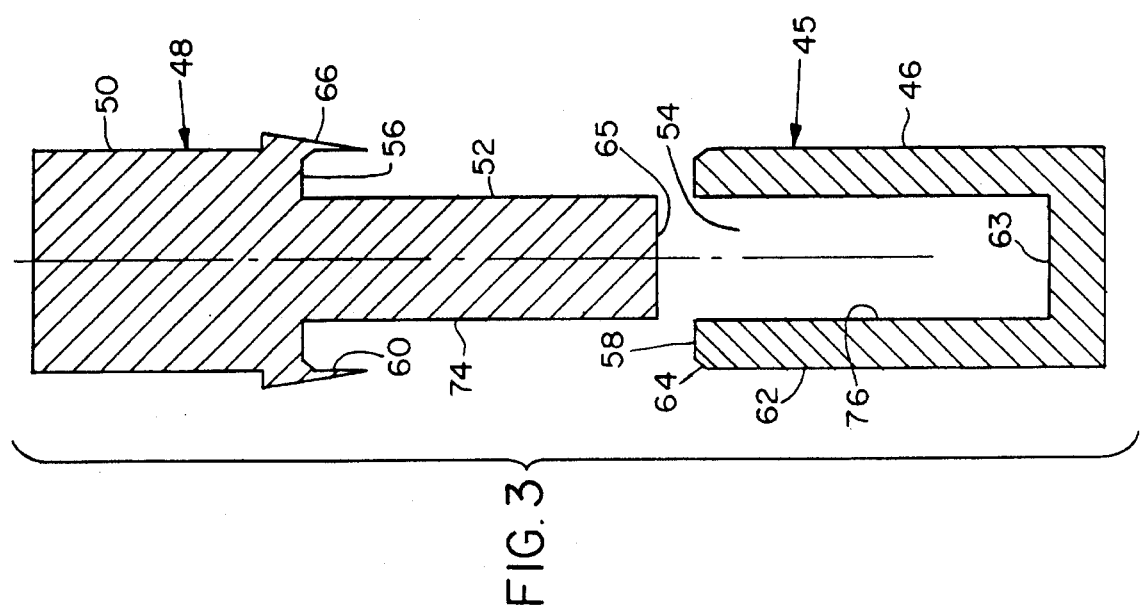
FIG. 3 is a cross sectional view of an alternative implant and post of this invention.

Referring to FIGS. 3, 4 and 5, implant 45 has central bore 54, top surface 58, bevel 64 and outside surface 62. Post 48 includes a top section 50, stem section 52, bottom surface 56 and circumferential collar 66 with internal surface 56, FIG. 3 shows the post 48 and implant 45 separately. FIG. 4 shows the post 48 partially seated into implant 45 having bottom section 46 and FIG. 5 show the post 48 fully seated into implant 45 of this invention. Stem 52 of post 48 is placed into central bore 54 of implant 45 and pressed into position until collar 66 engages bevel 64 of implant 45 so that bore wall 76 and the outside surface 74 of stem 52 are contiguous. As post 48 is further positioned downward into central bore 54 of implant 45, bevel 64 of implant 45 guides collar 66 into position. When the internal diameter of collar 66 is made to be slightly smaller than the external diameter of implant 45, bevel 64 will expand collar 66 to fit over outside wall 62 of implant 45 providing a tighter compressive fit. Stem section 52 is shown to be a frictional press fit though it could use any conventional method of joining a post to an implant such as threaded posts, screws, slots and wings, frictional extensions, taper fits, or the like.

FIG. 4 shows partial seating of post 48 into implant 45. If debris such as blood, saliva, tissue, bone or other objects are on the top surface 58 or bottom surface 63 of central bore 54 of implant 45, post 48 can not be fully seated. Similar results will occur if inaccuracy occurs during normal manufacturing techniques such as casting, machining, molding etc. and raised areas result on surfaces 56 or 65 of post 48 or surfaces 63 or 58 of implant 45. Without circumferential collar 66, the usual butt joint formed by top surface 58 of implant 45 and the bottom surface 56 of post 48 will result in an opening as wide as the debris between the two surfaces. The resulting opening produces failure of implants as bacteria forms infection within the open area.. With collar 66, an opening between bottom surface 56 of post 48 and the top surface 58 of implant 45 does not result in an opening between the post and implant interface as internal surface 60 of collar 66 of post 48 fits securely to wall 62 of implant 45. Thus failure of the implant due to bacteria collecting is avoided. Resistance to forces 70 and 72 occurs in the same manner as resistance to forces 11 and 31 discussed above.

Figure 7:
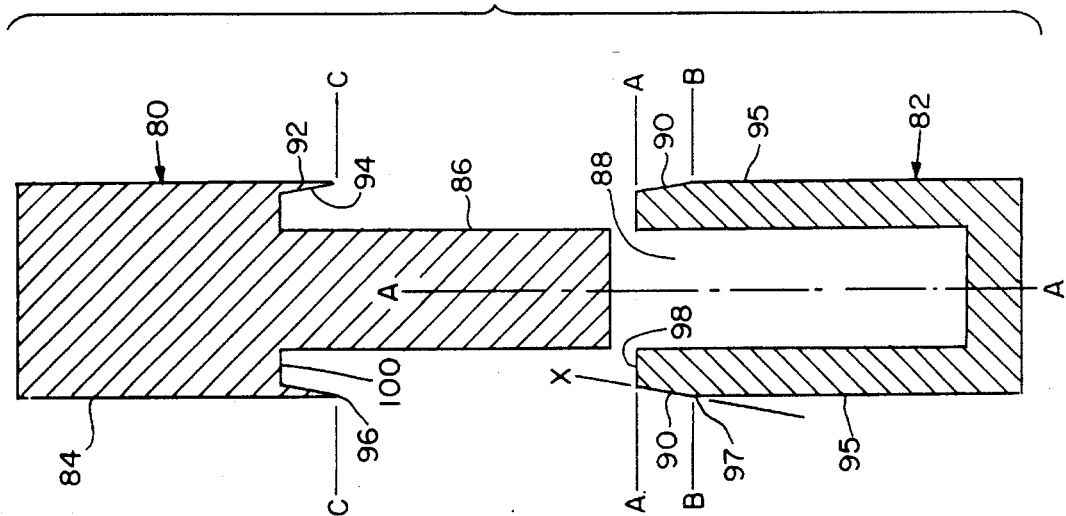
FIG. 7 is a cross sectional view of the implant and post of FIG. 6 disassembled.
Figure 6:
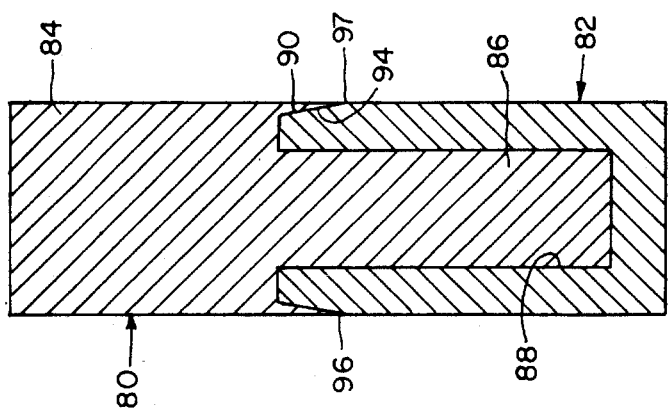
FIG. 6 is an cross sectional view of an alternative implant and post of this invention.

Referring to FIGS. 6 and 7, implant 82 has central bore 88, top surface 98 and external bevel 90. External bevel 90 of circumferential wall of implant 82 is constructed such that the diameter through line A—A is less than the diameter through line B—B which goes through point 97. Post 80 has stem portion 86, top section 84, groove surface 100, collar 92 with internal surface 94. FIG. 6 shows an assembled post 80 and implant 82 while FIG. 7 shows an unassembled post and implant. The outside surface 90 has an angle X—X between 0 and 25 degrees relative to vertical axis A—A. Stem section 86 of post 80 is inserted into central bore 88 of implant 82. The bottom surface 96 of collar 92 does not strike bevel surface 90 until post 80 is fully seated unless the post is not centered properly, then the bottom surface 96 of collar 92 is guided to position by beveled surface 90 of implant 82. When fully seated, bottom surface 96 of collar 92 meets with or is slightly above the junction 97 of bevel 90 and outside surface 95. When the diameter of the bottom surface 96 of collar 92 as observed through line C—C is smaller than the diameter of the contact area on the implant which would be junction 97 for example, expansion of collar 92 will occur and a tighter junction of the internal surface 94 of collar 92 to the outside beveled surface 90 of implant 82 will occur.

Figure 8:
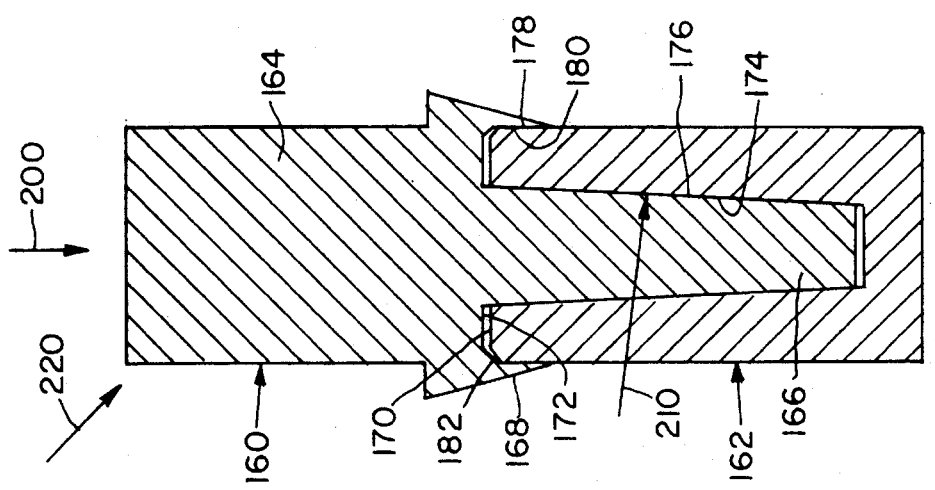
FIG. 8 is a cross sectional view of an alternative implant and post of this invention.

Referring to FIG. 8, tapered stem section 166 of post 160 is seated into a tapered central bore of implant 162. Frictional interaction of internal surface 174 of implant 162 to external surface 176 of post stem 166 provides retention for post 160 having top section 164 to implant 162. Groove surface 172 having bevel surface 182 of post 160 is constructed such that it can not contact top surface 170 of implant 162. This allows complete contact of external surface 176 of post stem 166 to internal surface 174 of implant 162 for complete retention which would not occur if surface 172 of post 160 contacted prematurely to top surface 170 of implant 162. Collar 168 which surrounds implant 162 provides a tight seal and less fracture potential. The contact of internal surface 180 of collar 168 to external surface 178 is tight because it slides on a vertical plane such the height of final position of post 160 within implant 162 is not critical to a tight seal of the post 160 to the implant 162. In addition, collar 168 provides resistance to implant 162 fracture. Forces 200 and 220 from function or parafunction, forces the tapered stem 166 of post 160 to act like a wedge resulting in force 210 from surface 176 of stem 166 pressing against surface 174 of implant 162 which can lead to implant 162 fracture. Resistance to force 210 is provided by surface 178 of implant 162 pressing against surface 180 of post 160 and therefore implant fracture is less likely to occur.

Figure 9:
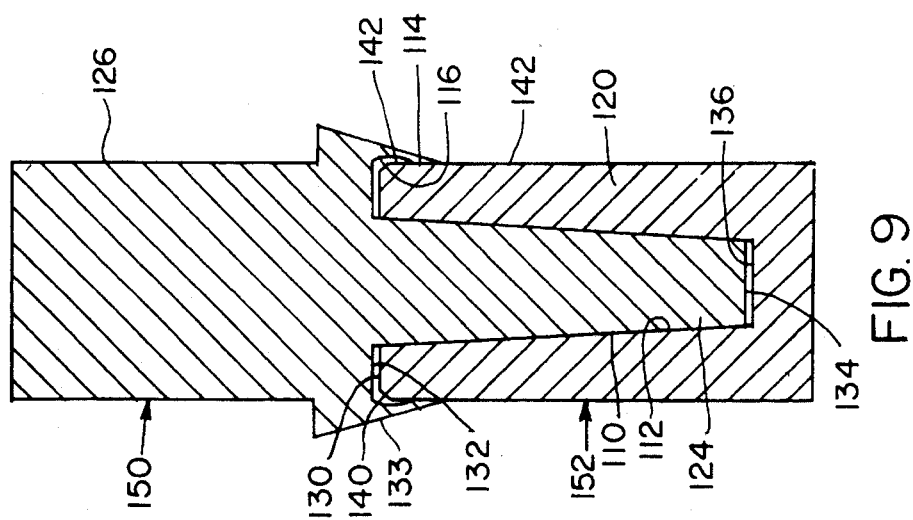
FIG. 9 is a cross sectional view of an alternative implant and post of this invention.

Referring to FIG. 9, post 150 having bottom section 124 and top section 126 is positioned within implant 152 having bottom section. The structure is similar to FIG. 8, however, collar 133 only contacts outside surface 142 of implant 152 at area 114 when bore wall 110 contacts outside surface 112 of bottom. Inside surfaces 116 and 132 of collar 133 does not contact outside surfaces 130, 140 and 142 of implant 152. Bottom surfaces 134 of post 150 does not contact bottom surface 136 of implant 152. This minimum contact allows easy placement of post 150 into implant 152 and still results in a tight seal. The collar 133 is easier to stretch around the outside of implant 152.

Figure 10:
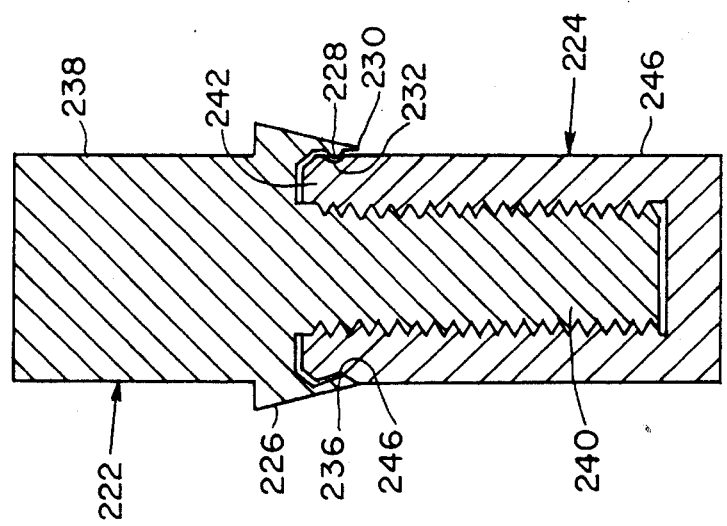
FIG. 10 is a cross sectional view of an alternative implant and post of this invention.

Referring to FIG. 10, post 222 has top section 238, threaded bottom section 240, and circumferential collar 226. Implant 224 has bottom section 246 and circumferential top section 242. Collar 226 of post 222 has end section 230 and intermediate section 228 and 236 which fit into indentation 232 and 246 of top section 242 of implant 224. During placement, sections 228 and 236 are compressed so that circumferential expansion of collar 226 will occur. Sections 236 and 228 of collar 226 of post 222 will interact with indented sections 246 and 232 of top section 242 of implant 224 to provide improved resistance to lateral forces over a simple vertical or beveled circumferential collar.

I claim:

1. A dental system for insertion into a bore of a jaw bone of a patient which comprises:

a dental implant adapted to fit in a bore of a jaw bone, said dental implant having a central hole extending from a top surface of said implant through a portion of the vertical height of said implant, said implant having a circumferential wall surrounding said central hole and having said top surface and a circumferential outside surface, a dental post having a stem section shaped to fit into said central hole and a circumferential collar, said collar having an internal diameter slightly smaller than the diameter of the circumferential outside surface, and means for positioning said collar over said top surface and over a portion of said outside surface to form a junction, said junction having an angle relative to a vertical axis of said implant of between 0 and 25 degrees.

2. The dental system of claim 1 wherein said means for positioning comprises a screw extending through a second central hole in said post and through at least a portion of said central hole of said implant.

3. The dental system of claim 2 wherein said outside wall is beveled.

4. The dental system of claim 1 wherein said junction has said angle between 0 and 10 degrees.

5. The dental system of claim 1 wherein said junction has said angle between 0 and 5 degrees.

6. The dental system of claim 1 wherein said outside surface includes a circumferential indentation and said collar includes a circumferential projection positioned to fit into said indentation.

* * * * *